(12) United States Patent
Vidal et al.

(10) Patent No.: US 7,342,217 B2
(45) Date of Patent: Mar. 11, 2008

(54) SYSTEM FOR THE MEASUREMENT AND DATA ACQUISITION FOR OPTICAL FIBER SENSORS

(75) Inventors: Jose Luiz Arias Vidal, Rio de Janeiro (BR); Manoel Feliciano da Silva Júnior, Rio de Janeiro (BR); Ricardo Munoz Freitas, Rio de Janeiro (BR); Lincoln Homero Thomé Ferreira, Rio de Janeiro (BR)

(73) Assignee: Petroleo Brasileiro S.A. - Petrobras (BR)

( * ) Notice: Subject to any disclaimer, the term of this patent is extended or adjusted under 35 U.S.C. 154(b) by 203 days.

(21) Appl. No.: 11/194,767

(22) Filed: Aug. 2, 2005

(65) Prior Publication Data
US 2006/0034558 A1    Feb. 16, 2006

(30) Foreign Application Priority Data
Aug. 10, 2004    (BR) .................................... 0403268

(51) Int. Cl.
    *H01J 5/16*    (2006.01)
(52) U.S. Cl. ........................... 250/227.14; 166/250.01; 166/254.2; 385/37
(58) Field of Classification Search ........... 166/250.01, 166/254.2; 385/12, 37; 250/227.14, 227.18
    See application file for complete search history.

(56) References Cited

U.S. PATENT DOCUMENTS

| | | | |
|---|---|---|---|
| 5,401,956 A | | 3/1995 | Dunphy et al. |
| 5,426,297 A | | 6/1995 | Dunphy et al. |
| 5,493,390 A | | 2/1996 | Varasi et al. |
| 5,513,913 A | * | 5/1996 | Ball et al. .................... 374/120 |
| 5,675,674 A | * | 10/1997 | Weis ........................... 385/12 |
| 6,097,487 A | * | 8/2000 | Kringlebotn et al. ........ 356/450 |
| 6,647,160 B1 | * | 11/2003 | Chi et al. ..................... 385/12 |
| 6,680,472 B1 | * | 1/2004 | Thingbø et al. ........ 250/227.12 |
| 6,816,638 B1 | * | 11/2004 | Bennion et al. .............. 385/13 |
| 6,913,079 B2 | * | 7/2005 | Tubel .................... 166/250.01 |
| 6,933,491 B2 | * | 8/2005 | Maida, Jr. .............. 250/227.14 |
| 2006/0157239 A1 | * | 7/2006 | Ramos et al. ............ 166/254.2 |

\* cited by examiner

*Primary Examiner*—Timothy Edwards, Jr.
(74) *Attorney, Agent, or Firm*—Nixon & Vanderhye PC

(57) ABSTRACT

A system for the measurement and surface data acquisition for optical fiber sensors containing Bragg gratings for the sensing of physical parameters originated from a set of oil wells, the system including: an optical system for signal processing, the signals being originated from physical parameters sensors installed in one single or in a set of oil and/or gas wells and resulting from the reflected wavelength in response to a perturbation of the physical parameter under measurement; an electronic system for signal processing for converting the optical intensity signals originated from the optical system into electrical signals with the aid of detectors that optimize the signal/noise ratio; and an optical switcher having an interface between a) and b), for expanding the number of monitored oil wells.

16 Claims, 6 Drawing Sheets

SYSTEM FOR THE MEASUREMENT AND DATA ACQUISITION FOR OPTICAL FIBER SENSORS

CROSS REFERENCE TO RELATED APPLICATION

This application is based upon, claims the benefit of, priority of, and incorporates by reference, the contents of Brazilian Patent Application No. PI 0403268-3 filed Aug. 10, 2004.

FIELD OF THE INVENTION

The present invention relates to a system for the measurement and data acquisition for optical fiber sensors, more specifically, to an interface for the measurement and data acquisition for Fiber Bragg grating temperature and pressure optical fiber sensors to be used in oil and/or gas wells.

BACKGROUND OF THE INVENTION

Since the seventies, when optical telecommunications based on sufficiently low attenuation were developed to allow the propagation of light to distances longer than 1 km, huge progress has been made in order to develop at the same time techniques using optical fibers designed for the measurement of a wide variety of physical, chemical and even biological quantities.

The main reasons for these efforts are some features inherent to optical fibers such as low weight, flexibility, long transmission distance, low reactivity, electrical insulation and electromagnetic immunity. Besides, there is in many cases the possibility of multiplexing the signals of several sensors, including those directed to the measurement of different quantities and even the possibility of carrying out measurements continuously distributed along the sensing fiber.

Optical fiber sensors are, therefore, optical sensors utilizing fibers as a connecting means for light between the mensurand and the measurement area. Optical fiber sensors can be divided between extrinsic and intrinsic. In the first category are those where the fiber is only a waveguide and the optical effect to be measured occurs out of the fiber. In the second case the fiber is also a medium where the coupling between the mensurand and the light occurs, this rendering this kind of sensor more practical under the mechanical point of view. Sensors can also be considered as for the kind of optical effect to be measured, such as a change in intensity, in polarization, in the spectrum or in the phase of the light wave.

Since the nineties a new component is becoming more and more important not only in telecommunications but also in various applications in the sensor field. This component, called fiber Bragg grating (FBG) is nothing more than a reflective optical fiber having an extremely high spectral selectivity. Its setup is based in the generation of a periodical modulation in the refractive index of the fiber core, such structure being able to efficiently reflect the $\lambda_b$ wavelength satisfying the first order Bragg condition for normal incidence, that is, equation (1) below:

$$\lambda_b = \Lambda/2n \quad (1)$$

where $\Lambda$ is the spatial period of the index modulation and n is the refractive index of the fiber.

The sensing ability of the Bragg gratings is related to the fact that $\lambda_b$ can be altered by mechanical efforts modifying the structure periodicity, $\Lambda$, or through temperature that modifies the refractive index n. Such dependencies can be approximately summarized in the expression of equation (2) below:

$$\Delta\lambda_b/\lambda_b = 9 \times 10^{-6} \Delta T + 0.78\epsilon \quad (2)$$

Where $\Delta T$ is measured in degrees Centigrade (° C.) and $\epsilon$ is dimensionless (m/m). The numerical constants are those typical of the material of which the fiber is made up, and particularly, the thermal constant, can vary depending on the fiber.

The information provided by FBG's is contained in spectra, which renders the measurement an absolute, easy to multiplex quantity and makes Bragg gratings particularly attractive for use in sensors.

For usual wavelengths (1300 nm and 1550 nm) equation (2) implies that the measurement of $\lambda_b$ should be performed at an accuracy of the order of 1 pm in order to obtain an accuracy of 1 ppm (1 µm/m) strain or 0.1° C. in temperature. There are several ways of reaching this objective, as will be seen below.

Based on the modifications brought about in the fiber Bragg grating optical spectrum of reflection, different procedures can be employed for the measurement of strains or temperature changes. The choice is not an obvious one and chiefly depends on the desired application, and for each case one must consider the frequency bands involved, the number of interrogated sensors, their spatial distribution, the dynamic range of strains or temperatures to be measured, space and weight limitations imposed by the measurement system and, for sure, the cost involved.

Some of the most widely used techniques for the measurement of Fiber Bragg grating sensors are those that use adjustable band filters for the sweeping of the optical spectrum. To this context belongs the simplest technique consisting in the direct measurement by means of an Optical Spectrum Analyzer (OSA).

It is possible to obtain a resolution in the 1 pm range in the spectrum measurement, which corresponds to strains close to 1 µm/m or 0.1° C. temperature changes. The dynamic range for strain measurements is limited according to the number of interrogated sensors. By using two LEDs in the typical wavelengths of 1300 nm and 1550 nm, the relationship between the dynamic range, $\Delta\epsilon$, and the number of sensors, N, can be estimated by means of the relationship below (equation (3)):

$$\Delta\epsilon = 10^5/N \text{ (in µm/m)} \quad (3)$$

Thus, for example, for the measurement of one hundred sensors using a commercial OSA, the dynamic range estimated for each measurement site is of the order of 1,000 µm/m. The main advantage of using a general purpose OSA is the simplicity and quick setting of the measurement system. However, the high cost of the equipment should be considered as well as the slowness at which is carried out the sweeping of the optical spectrum—typically, one sweeping per minute at a range of 100 nm, which practically restricts its use to static measurements. Therefore such technique should in general terms be considered for situations where the measurements are not permanent so that the equipment can be employed for additional applications. In case it is desired to measure a huge number of sensors in the same fiber, such alternative can become economically attractive.

Further, it should be pointed out that such equipment can be utilized as a fixed filter system, similar to that which will be discussed later on in the present specification. This way of utilization allows obtaining dynamic measurements (a few hundreds of Hz) but certainly should not be used in a continuous mode in view of the equipment cost. Finally, a very interesting feature is the easy calibration that can be performed, either continuously or periodically, by introducing a wavelength reference that can be made up of a gas cell or a Bragg grating in a thermally compensated encapsulation.

Fabry-Perot filters having the spectral band determined by a cavity that can be dynamically altered by for example, piezoelectric actuators, are also used for performing spectral sweepings. In an optical circuit that can be employed together with an adjustable pass band Fabry Perot filter the pass band is made to vary in an alternate way through linear slopes, so that each of the interrogated sensors is sequentially illuminated. Resolutions close to 1 µm/m can also be obtained through the use of this technique. The sweeping of such filters is typically limited to nearly 100 nm, the frequency response hardly being higher than a few tens of Hz.

Analogously to the previous case, the cost of this technique does not depend on the number of sensors to be interrogated, this rendering it more competitive as the number of measured sites is increased.

For systems having a not very large number of sensors, a lower cost alternative employs fixed spectral filters. Such filters can be of the Fabry-Perot kind, Mach Zender interferometer, or even a Bragg grating as in the case of the present invention. FIG. 1 attached shows optical circuits using this technique. The system employs broadband sources and the signal reflected by the grating used as sensor is directed, through a 3 dB coupler, to the filter and to a reference detector. The optical signal resulting from the interaction with the filter is then guided towards the other detector, and its electrical outlet it divided by the one obtained by the reference detector. The utilization of a reference signal aims at compensating fluctuations in the optical source. As explained in more detail hereinbelow, it was experimentally found that the proposed implementation allows the measurement signal to be kept stable, with a change lower than ±0.5% while the power supplied by the LED is reduced in up to 30%. The topologies proposed for the measurement of four sensors, illustrated in FIG. 1 attached to the present specification, can be sufficiently extended to up to 16 sensors without any apparent technical problems. The utilization of two sources makes the system more robust. The cost for implementing the solutions proposed in FIG. 1 is rather low for the measurement of just one sensor when compared to the acquisition of previously described equipment. As more channels are added to the system such cost increases linearly.

Besides the modularity, another important advantage in the utilization of fixed spectral filters is the possibility to apply such devices in dynamic measurements. The frequency range is limited by the photodetector's response and can easily reach a few hundreds of kHz. The computational modeling of the reflection of a broadband optical signal by the sensor and then by the filter means that smaller uncertainties are obtained by using two gratings (sensor and filter) having identical spectra. Uncertainty and resolution are dictated by the photodetector frequency response. Based on simulated data it is possible to estimate that for measurements in a 10 Hz band, uncertainties of ±0.1% would be obtained in a dynamic range of ±1,500 µm/m.

A further set of procedures potentially applicable to the measurement of systems requiring the interrogation of several sensors is that based on time multiplexing.

One possibility in this area consists in the utilization of an OTDR—Optical Time Domain Reflectometer. The sensing gratings, which can be written in a same wavelength and in a same optical fiber, should bear low reflectivity, of the order of 1%. However, it should be pointed out that in view of the working principle of an OTDR the utilization of this technique is limited to static measurements.

Among the above-mentioned techniques, doubtless the fixed filter system is the cheapest available for a small number of sensors and it is also the system having the quickest response, with the possibility of reaching several kHz according to the electronic system. Thus, the surface data acquisition system disclosed hereinbelow in the present specification employs a fixed filter system where the filters are made up of Bragg gratings.

U.S. Pat. No. 5,401,956 teaches a practical diagnosis system working in cooperation with remote optical fiber sensors containing Bragg gratings for measuring static strain, dynamic strain and/or acoustic/vibratory perturbations of items or structures.

U.S. Pat. No. 5,426,297 teaches a system allowing a plurality of Bragg grating sensors in one single fiber as well as in a plurality of fibers, each one having a plurality of Bragg gratings to be detected, such system detecting each of the wavelengths and shifts of the same reflected by the Bragg grating.

U.S. Pat. No. 5,493,390 teaches a system involving a source of light, an optical fiber containing a Bragg grating forming a sensor reflecting a wavelength in response to a perturbation, integrated tunable opto-acoustical filter placed in the path of the light emitted by said sensor for filtering the light received from the sensor, the filter pass band being adjustable to superimpose to the reflection wavelength of the sensor in response to a control signal of the filter, and to provide a filtered signal the power of which is related to the optical transmission; optical detection device for detecting the power of the filtered signal and providing a detection signal and a device for signal processing in response to the detection signal for providing the filter control signal, detecting a shift in the reflection wavelength caused by the perturbation, the signal processing device including devices for adjusting the filter control signal to follow static shifts in the reflection wavelength and dynamic shifts in the sensor wavelength caused by static and dynamic shifts in the perturbation, for a predetermined length of time, and for providing output signals able to indicate the static and dynamic shifts in the perturbation.

In spite of the approaches provided for by the state-of-the-art technique, there is still the need of a system for the measurement and surface data acquisition for fiber Bragg grating-based optical fiber pressure and temperature sensors, said system comprising: i) an optical system for signal processing with an optical source transmitting a signal through an optical coupler, said signal being conveyed to fiber Bragg grating (FBG) optical fiber sensors, the optical signals returning from said optical fiber sensors passing by couplers and divided in outputs so as to yield reference signals conveyed to detectors; ii) an electronic signal processing system, and iii) an optical switcher with an interface, connecting the optical fiber sensors containing Bragg gratings for the measurement of physical parameters such as pressure and temperature in an oil and/or gas well and the optical and electronic systems, such system for the measurement and data acquisition being described in the present application.

SUMMARY OF THE INVENTION

Broadly, the present invention comprises a system for the measurement and surface data acquisition for optical fiber sensors containing Bragg gratings for the sensing of physical parameters originated from a set of oil wells, said system comprising:

a) an optical system for signal processing, said signals being originated from physical parameters sensors installed in one single or in a set of oil and/or gas wells and resulting from the reflected wavelength in response to a perturbation of the physical parameter under measurement;

b) an electronic system for signal processing for converting the optical intensity signals originated from said optical system into electrical signals with the aid of detectors that optimize the signal/noise ratio; and c) an optical switcher having an interface between a) and b), for expanding the number of monitored oil wells.

Thus, the invention provides a system for the measurement and surface data acquisition for fiber Bragg grating pressure and temperature optical fiber sensors to be applied in oil and/or gas wells.

Still, the invention provides a system for the measurement and surface data acquisition for fiber Bragg grating pressure and temperature optical fiber sensors where lower uncertainties are obtained by utilizing two gratings (sensor and attenuator) having identical spectra.

The invention provides further a system for the measurement and surface data acquisition for fiber Bragg grating pressure and temperature optical fiber sensors made up of an optical system for signal processing, an electronic system for the processing of said signals and an interface provided with an optical switcher between the optical system and the electronic system.

The invention provides also a system for the measurement and surface data acquisition for fiber Bragg grating pressure and temperature optical fiber sensors that attends to the demand for the monitoring of pressure and temperature in wells, for the acquisition of dynamic data.

BRIEF DESCRIPTION OF THE DRAWINGS

FIG. 1 attached illustrates state-of-the-art optical circuits utilizing Bragg gratings as fixed pass band filters.

DETAILED DESCRIPTION OF THE PREFERRED MODE

The invention relates therefore to a system for the measurement and surface data acquisition for fiber Bragg grating pressure and temperature optical fiber sensors to be utilized in oil and/or gas wells, the system being made up of an optical system for signal processing, an electronic system for processing said signals and an optical switcher with an interface between said optical system and said electronic system.

The data acquisition system is suitable for utilization in oil and/or gas wells. It should be pointed out that the suggested setup throughout the specification for the acquisition system is made up of individual modules that can be configured into different setups and that these setups can be expanded, according to the acquisition scope and the number of sensors.

The invention will now be described by reference to the attached Figures.

Figure 1A:
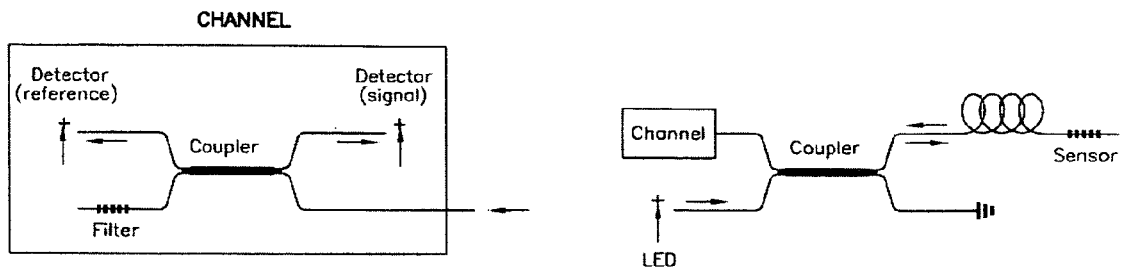
FIG. 1A attached shows the measurement channel and the circuit for one sensor.
Figure 1B:
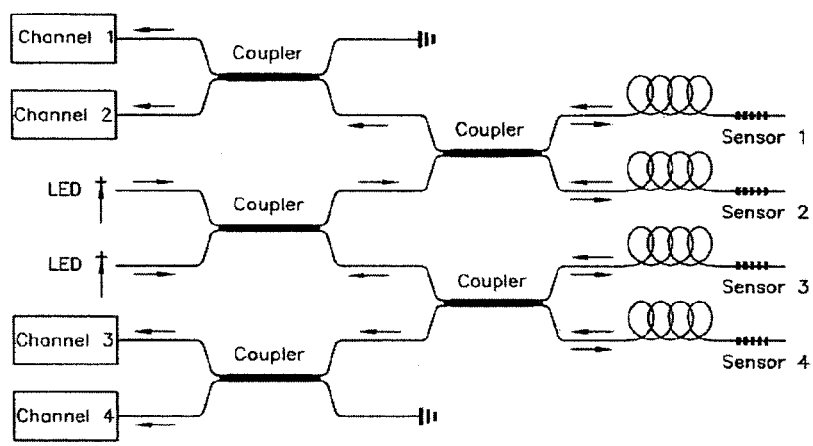
FIG. 1B illustrates a circuit for four sensors in different fibers and FIG. 1C shows the circuit for four sensors in one single fiber.
Figure 1C:
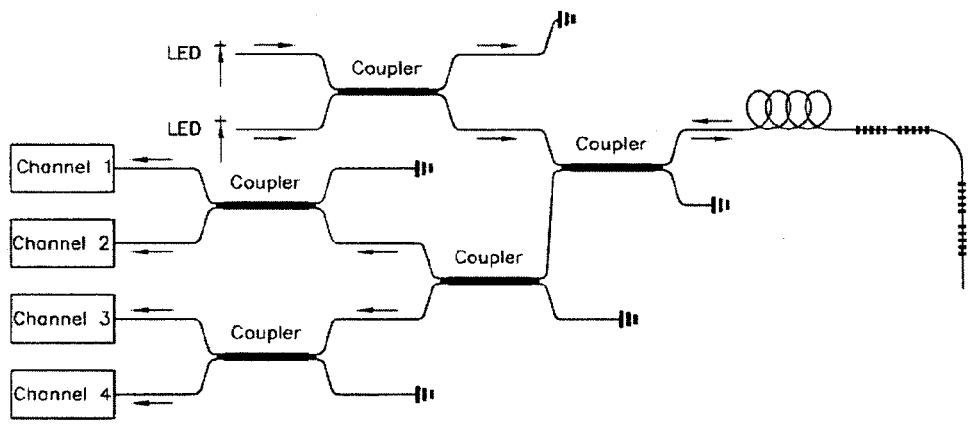

FIG. 1 is a diagram that illustrates state-of-the-art optical circuits using Bragg gratings as fixed pass band filters. FIG. 1A shows the measurement channel and the circuit for one sensor. FIG. 1B shows a circuit for four sensors in different fibers while FIG. 1C shows the circuit for four sensors in one single fiber.

Figure 2:
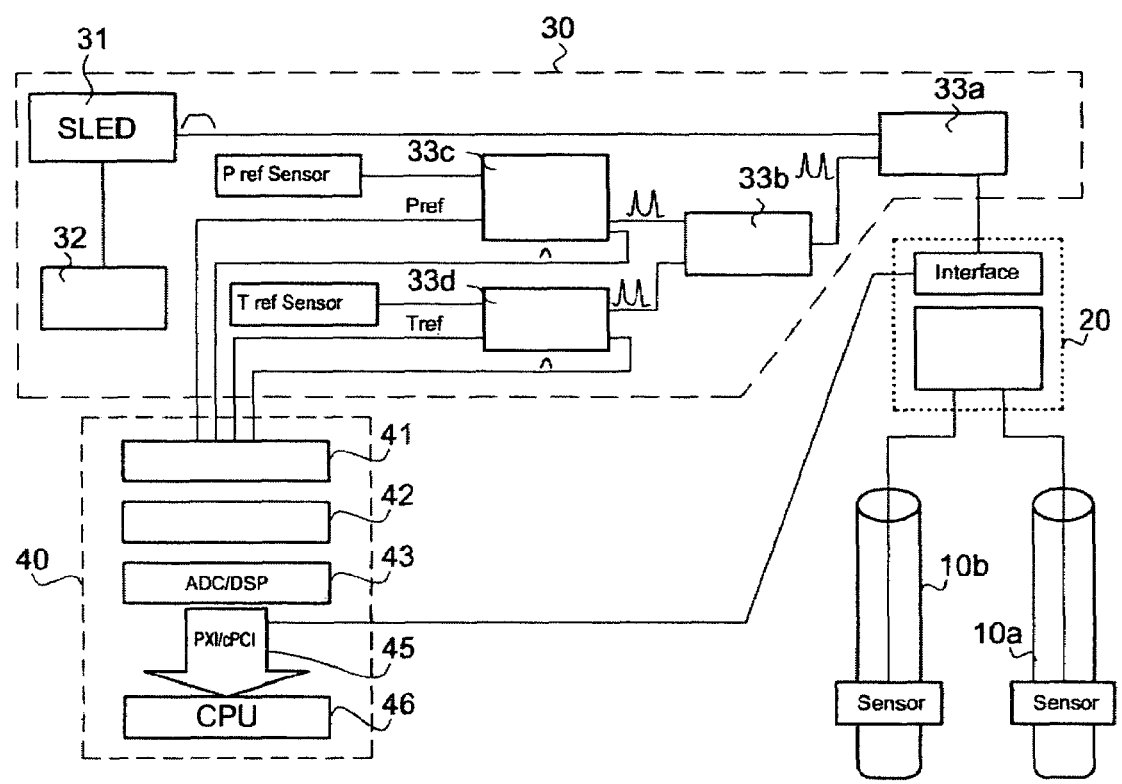
FIG. 2 attached is a scheme of the data architecture and control for oil wells based on optical fiber sensors.

FIG. 2 is a general scheme of the surface acquisition data system for oil and/or gas wells presented in the invention. Thus, pressure and temperature optical fiber sensors (10a) and (10b) containing Bragg gratings are inserted in oil wells. In optical module (30) an optical source (31) connected to a modulator (32) conveys light through a coupler (33a) and an optical switcher (20) up to pressure and temperature sensors (10a) and (10b) in the oil wells. The parameters measured by sensor (10a) and by sensor (10b) are conveyed to an electronic module (40) where they are processed and converted into electrical signals through detectors that optimize the signal/noise ratio.

In order to obtain the lowest uncertainties in the measurements, two Bragg gratings should be used, that is, the sensor grating and the filter grating having identical spectra.

Figure 3:
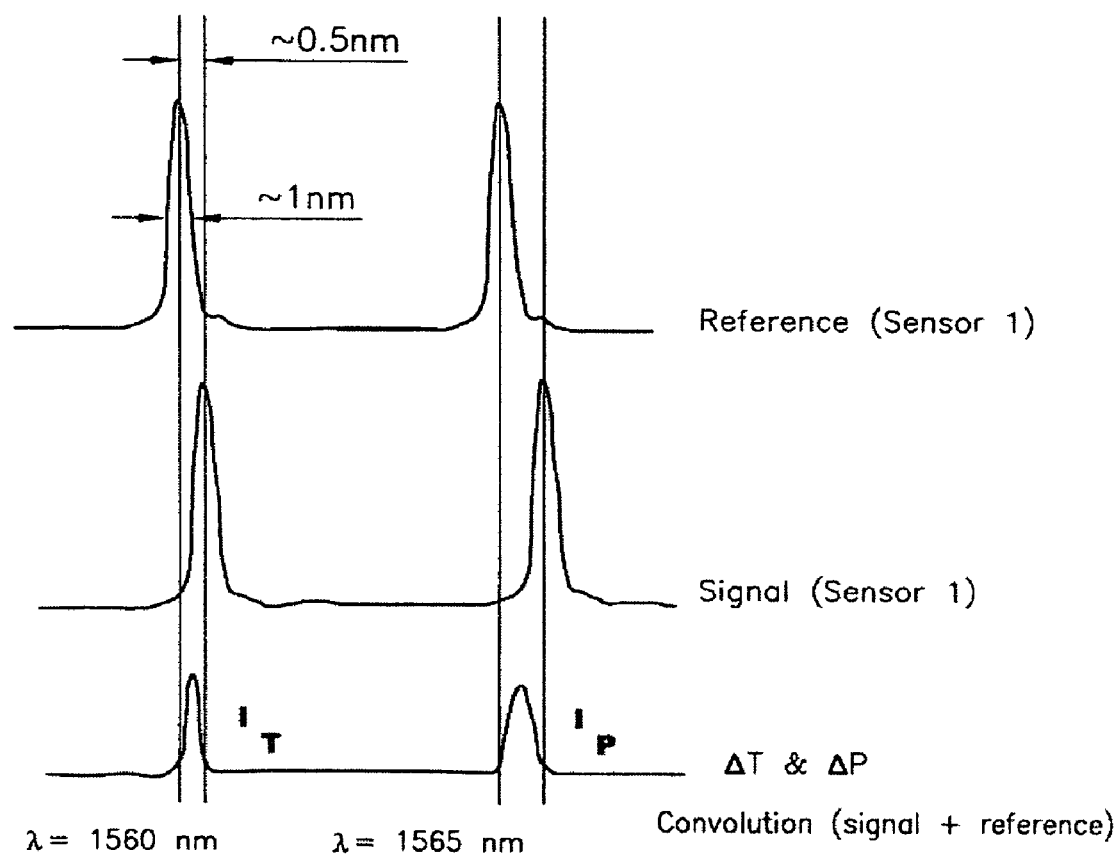
FIG. 3 attached is a series of graphs representing the convolution between the sensor signals and those of the reference.

FIG. 3 illustrates a graph for the convolution between the signals of one sensor (10a/10b) and those of the reference, that is, the comparison between the optical signals from the sensors of each channel and from their respective reference gratings. Therefore, possible fiber attenuations and changes in optical power emitted by optical source (31) are automatically compensated through the ratio between the signal directly received from the sensor (10a/10b) and the signal resulting from the convolution between signals.

Figure 4:
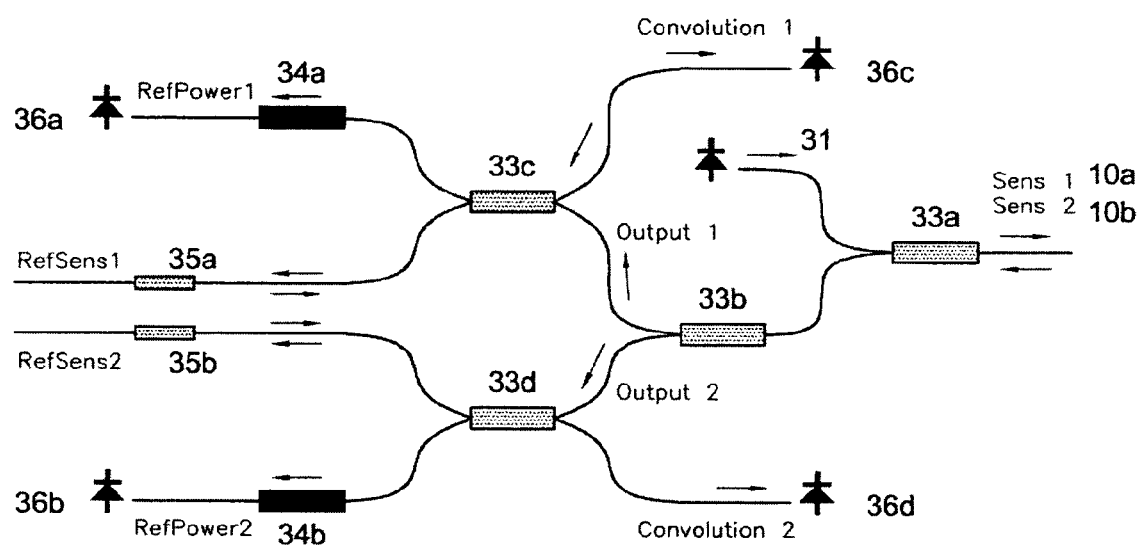
FIG. 4 attached is a diagram of the optical circuit according to the invention.

FIG. 4 illustrates the details of the optical module (30) used in the invention.

Optical source (31) is based on a super luminescent diode (SLED), the power of which is 5 mW. The power is amplitude-modulated by a 1 KHz sinusoid signal, and is transmitted in one of the arms of an optical coupler (33a). The optical signal generated by source (31) is conveyed to two optical fiber sensors (10a/10b) containing fiber Bragg gratings. Sensors (10a/10b) are designed for the measurement of pressure and temperature of oil and/or gas wells and can be any commercial pressure and temperature optical fiber sensors containing fiber Bragg gratings. The return of the optical signal of the two sensors (10a/10b) crosses a coupler (33b) that divides the signal into two outputs, (Output 1) and (Output 2).

The optical signal of the first output (Output 1) is directed to another coupler (33c) that divides said signal into two other outputs: that of channel 1 power reference signal (RefPower 1) and that of channel 1 sensor reference signal (RefSens 1).

The optical signal of the second output (Output 2) is also directed to another coupler (33d), performing a processing analogous to that of Output 1, that is, it divides the signal into two further outputs: that of channel 2 power reference signal (RefPower 2) and that of channel 2 sensor reference signal (RefSens 2).

Channel 1 power reference signal (RefPower 1) is conveyed to a sensor detector (36a) by means of a 20 dB fixed attenuator (34a).

Analogously, channel 2 power reference signal (RefPower 2) is conveyed to a sensor detector (36b) by means of a 20 dB fixed attenuator (34b).

The correction of the dynamic range of the power ratio is obtained through utilization of attenuators (34a, 34b).

Sensors detectors (36a through 36d) are based on PINFET technology.

Sensor detector (36c) receives the signal from the convolution between the signal reflected by sensor 1 (Sens 1) and the inner fixed reference (35a) (RefSens1).

Analogously, sensor detector (36d) receives the signal from the convolution between the signal reflected by sensor 2 (Sens 2) and the inner fixed reference (35b) (RefSens2).

The inner reference gratings (35a, 35b) are kept at constant temperature by the use of a thermoelectric temperature controller (non-represented).

In short, for the calculation of the parameters measured by sensor 1 (10a), one evaluates the ratio between the optical intensity of the signal of sensor detector (36c) (convolution 1) and that of sensor detector (36a) (channel 1 power reference—RefPower1).

Analogously, for the calculation of the parameters measured by sensor 2 (10b), one evaluates the ratio between the optical intensity of the signal of sensor detector (36d) (convolution 2) and that of sensor detector (36b) (channel 2 power reference—RefPower2).

Figure 5:
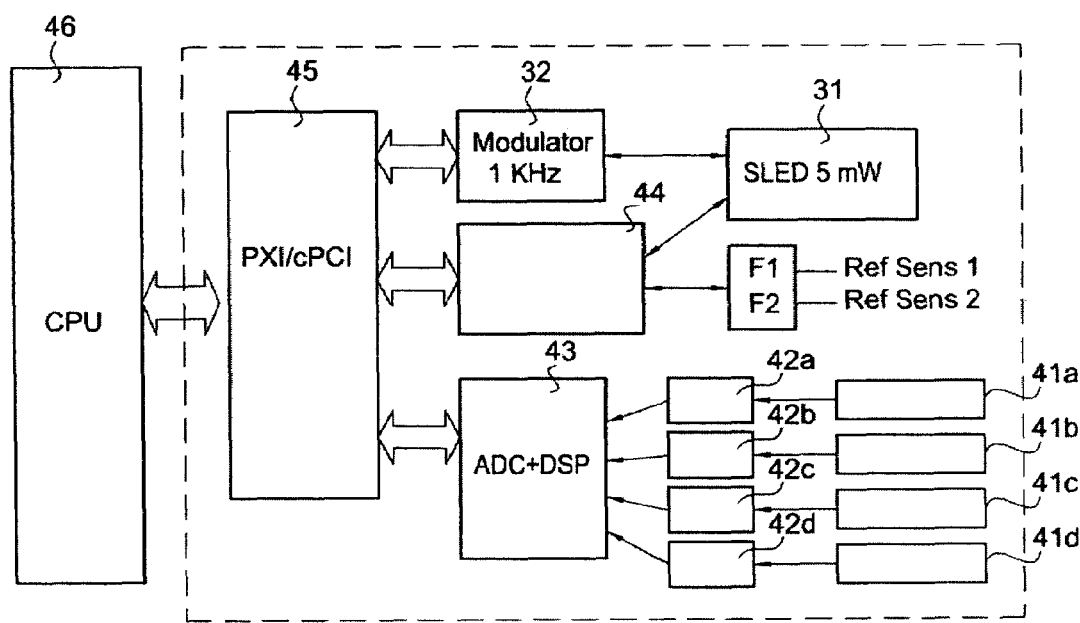
FIG. 5 attached is a block diagram of the electronic system.

FIG. 5 details the module (40) for electronic signal processing.

In module (40), the optical intensity signals are converted into electrical signals through detectors (41a, 41b, 41c, 41d) that optimize the signal/noise ratio. These detectors are also of the PINFET type.

Aiming at rendering detection circuits immune to the offset tensions of the input electronic circuits so as to obtain a thermally stable measurement system and making possible the exact measurement of very low powers, one uses the amplitude modulation by a 1 KHz sinusoid signal at the optical source (31) and respective demodulation in detecting circuits (41a, 41b, 41c, 41d).

Electrical signals resulting from detectors (41a, 41b, 41c, 41d) are conditioned and filtered with the aid of low pass filters (LPF) (42a, 42b, 42c, 42d). Then, the signals are converted to digital form using an analog-digital converter (A/D) at a rate of 64 kbits/s, so that a digital signal processor (DSP) (43) processes the signals.

DSP (43) allows the calculation of the ratio of the two power signals already converted from analog to digital in each sensor (10a, 10b) and the synchronous detection of the two signals resulting from the ratio (intensity peaks) through a Fast Fourier Transform (FFT) with the Hanning window.

In order to improve the dynamic range by the need of a more powerful and stable source of light it is recommended to utilize a temperature-stable super luminescent diode (SLED) (31), the temperature being stabilized with the aid of a TEC (Thermo Electric Cooler—Peltier) (44).

The same temperature-stabilizing effect is obtained in the inner reference fixed filters (F1 and F2) using TEC. Through the temperature control the repeatability of measurements is assured.

The PXI/cPCI (45) aims at converting data from related optical intensity measurements with the changes in physical quantities, said data being digitalized by the Analog Digital Converter (ADC) of the Digital Signal Processor (DSP) towards the CPU via standard industrial PXI backplane for further processing.

CPU (46) allows processing the optical intensity signals collected from the sensors (reference electrical signals, and source of light converted and digitalized) with data of the specific calibration curves for each sensor (10a, 10b) rendering such correlation into physical magnitudes such as pressure and temperature, the control of the equipment working status and the communication with the outer device) (controller or supervising system).

Figure 6:
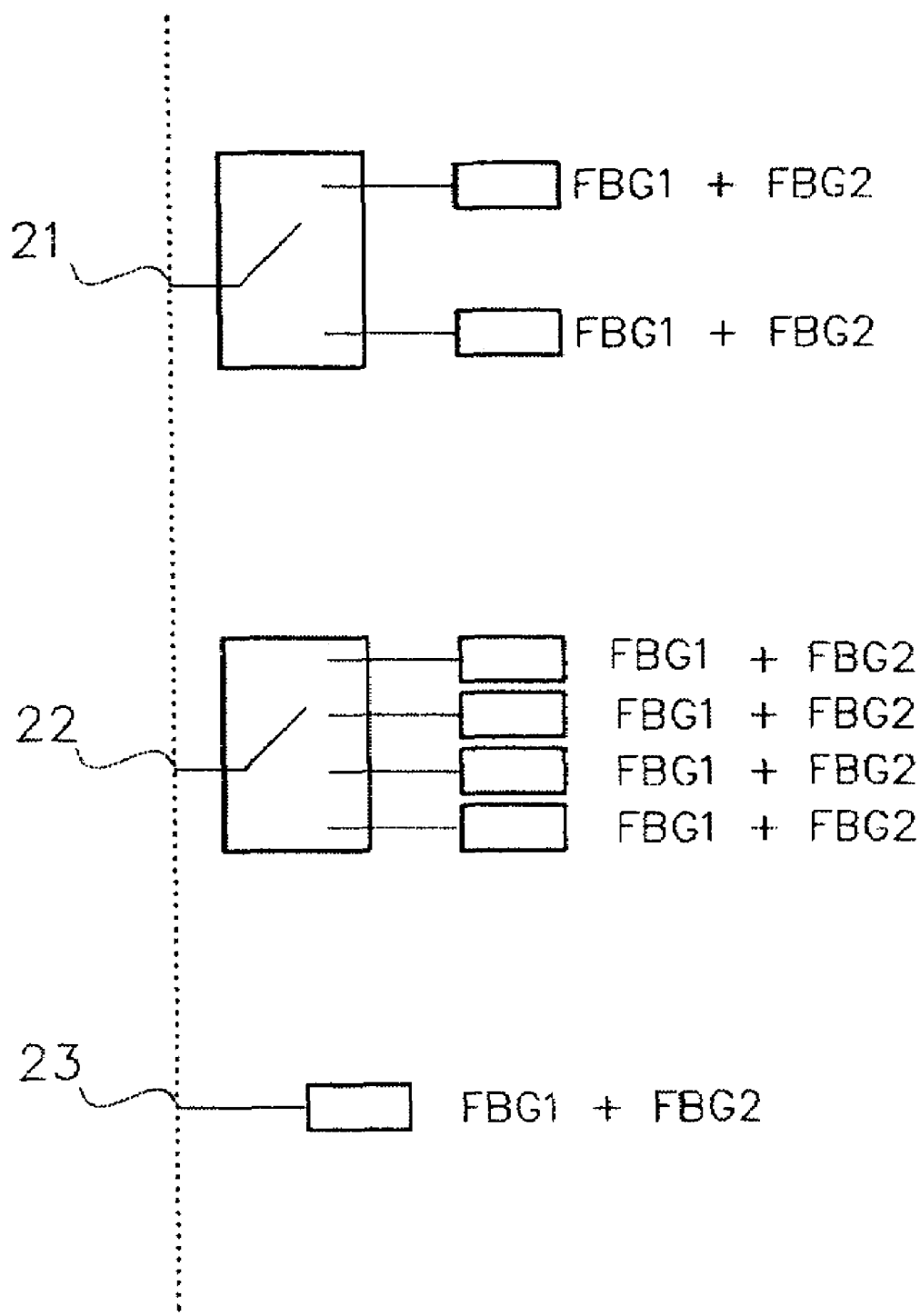
FIG. 6 attached is a block diagram illustrating the several possible arrangements of the optical switcher module.

FIG. 6 schematically details the modes of module (20) of the optical switcher: multiplexed in 1:2 (21), 1:4 (22) and (23) without switcher. The outer optical switches are controlled by system CPU (46) and allow to expand the number of monitored wells, in this case up to four wells at the same time, provided the gratings of all sensors have the same wavelength and shape (matched to the reference filters) of the inner references (reference FBG filters of the equipment).

The multiplexing options of the optical switchers have at least ten million cycles useful life and are controlled from outside by a serial signal.

It should be pointed out that all the circuits (detectors and sources of light) are setup in one single printed circuit board in order to attend to the compaction requirement.

The objective of the measurement and data acquisition system of the invention is to be used in an industrial environment (well surface) so as to secure the main features of the system: robustness, compaction and noise immunity EMI/RFI As an integral part of the system, it is worthwhile to mention the developed software, which includes signal processing (FTT with Hanning window) in DSP (43), calibration curves, status and management of the system working in CPU (46)

The working of the proposed system is based on the relative measurement of the optical power, since what is processed is the ratio between the signals from each optical sensor element and its respective reference channel.

The use of modulation techniques of the optical source and the respective demodulation in the detecting circuits allow to reach reduced off-set levels, this being an important factor to obtain long-term stability of the measurement system.

The use of reference channels in the receptor circuits allows the automatic compensation of possible attenuations of the sensor-containing fiber, as well as changes of the emitted optical power.

The advantage in the implementation of the fixed filter with optical power reference technique is the amplitude modulation of the optical source with synchronous detection of the signals resulting from the Fast Fourier Transform, that is, the manner for the measurement of the physical magnitudes of the optical pressure and temperature (P&T) sensors involves the indirect correlation of the wavelength change into intensity change as received from each grating (sensor).

The method for measurement and return processing (light) is effected by means of the basic processing of the following parameters: measurement of source intensity, measurement of inner references resulting from each surface FBG filter, and correlation of the optical signal received from sensor (FBG filter) and its reference grating at the surface (relationship between the signal received from a grating without change in strain and temperature, with a grating/sensor with change in temperature and strain). The optical source is amplitude-modulated, and the signal of electric response is detected by processing with the aid of FFT (Fast Fourier Transform).

The present system is provided with the following advantages:

- it comprises circuits (detectors and sources of light) mounted in one single printed circuit board in order to comply with compaction requirements;
- a more powerful and stable source of light is employed, aiming at improving the dynamic range using a SLED with temperature stabilization;
- the use of PINFET detectors leads to non susceptibility to interferences;
- the optical filters with temperature control allow to secure the repeatability of the circuit;
- DSP (43) and CPU (46) allow the processing, measurement, storing and communication with the outer and supervisory controller; possible fiber attenuations while changes of the emitted optical power are automatically compensated;
- The system provides analog signals compatible with the A/D plate to which it is coupled;
- It is possible to obtain very exact measurements of low optical powers;
- The system is shielded against EMI/RFI interferences.

We claim:

1. A system for the measurement and surface data acquisition for optical fiber sensors containing fiber Bragg gratings for the sensing of physical quantities originated in one oil and/or gas well or in a set of oil and/or gas wells, wherein said system comprises: an optical system (30) with an optical source (31) connected to a modulator (32) for conveying light through a coupler (33a) and an optical switcher (20) to sensors (10a, 10b) for sensing physical parameters in the oil and/or gas wells, signals originating from sensors (10a, 10b) being directed to an electronic module (40), where they are processed and converted into electrical signals through detectors (36a, 36b, 36c, 36d) that optimize the noise/signal ratio, the system being constructed and arranged for:

a) transmitting the optical signal generated by source (31) to one of the arms of an optical coupler (33a) and conveying said signal to sensors (10a, 10b), the return of the optical signal of the two sensors (10a, 10b) crossing a couple (33b) that divides the signal into two outputs, (Output 1) and (Output 2);

b) directing the optical signal of the first output (Output 1) to a further coupler (33c), said signal being divided in two further outputs: channel 1 power reference signal (Ref Power1) and channel 1 sensor reference signal (RefSens1);

c) in a way analogous to that of b), also directing the optical signal of the second output (Output 2) to a further coupler (33d), and dividing said signal in two further outputs; channel 2 power reference signal (RefPower 2) and channel 2 sensor reference signal (RefSens2);

d) conveying channel 1 power reference signal (RefPower1) to a detector (36a) through a fixed 10 dB attenuator (34a);

e) conveying in a way analogous to d), channel 2 power reference signal (RefPower2) to a detector (36b) through a fixed 10 dB attenuator (34b);

f) arranging for detector (36c) to receive the signal from the convolution between the reflected signal of sensor 1 (Sens1) and the inner fixed reference (35a) (RefSens1); and g) arranging in a way analogous to f), detector (36d) to receive the signal from the convolution between the reflected signal to sensor (Sens2) and the inner fixed reference (35b) (RefSens2).

2. A system according to claim 1, wherein the signals result from reflected wavelength in response to pressure and temperature measurements.

3. A system according to claim 1, wherein the gratings of sensor (10a/10b) and fixed attenuator (34a/34b) have identical spectra.

4. A system according to claim 1, wherein said sensors (10a, 10b) are designed to measure pressure and temperature of oil and/or gas wells.

5. A system according to claim 1, wherein said sensors (10a, 10b) are sensors using Fiber Bragg grating technology wherein the reference gratings and the sensor gratings have the same spectrum.

6. A system according to claim 1, wherein said optical source (31) is based on a 5 mV power super luminescent diode SLED, said diode being amplitude-modulated by a 1 kHz sinusoidal signal.

7. A system according to claim 1, wherein the inner reference gratings (35a, 35b) are kept at constant temperature through the use of a thermoelectric temperature controller TEC.

8. A system according to claim 1, wherein for the calculation of the parameters measured by sensor 1 (10a), one evaluates the ratio between the optical intensity of the signal of detector (36c) (convolution1) and that of detector (36a) (channel 1 power reference—Refpower1).

9. A system according to claim 1, wherein for the calculation of the parameters measured by sensor 2 (10b), one evaluates the ratio between the optical intensity of the signal of detector (36d) (convolution2) and that of detector (36b) (channel 2 power reference—RefPower2).

10. A system according to claim 1, wherein the correction of the dynamic range of the power ratio is given by the utilization of the attenuators (34a, 34b).

11. A system according to claim 1 wherein in the electronic module (40), the optical intensity signals are converted into electrical signals through detectors (41a, 41b, 41c, 41d) that optimize the signal/noise ratio.

12. A system according to claim 11, wherein amplitude is modulated by a 1 KHz sinusoidal signal in optical source (31) and the respective demodulation is carried out in detecting circuits (41a, 41b, 41c, 41d).

13. A system according to claim 11, wherein the electrical signals resulting from said detectors (41a, 41b, 41c, 41d) are conditioned and filtered with the aid of low pass band filters (LPF) (42a, 42b, 42c, 42d) and then converted into digital form by means of an analogical/digital converter (A/D), at a 64 kbits/s rate, to be processed by a digital signal processor (DSP) (43).

14. A system according to claim 1, wherein said optical switcher module (20) comprises multiplexing (21) for two sensors.

15. A system according to claim 1, wherein said optical switcher module (20) comprises multiplexing (22) for four sensors.

16. A system according to claim 1, wherein said optical switcher module (20) is free from multiplexing (23).

* * * * *